United States Patent [19]

Coates

[11] Patent Number: 5,405,395
[45] Date of Patent: Apr. 11, 1995

[54] MODULAR FEMORAL IMPLANT
[75] Inventor: Bradley J. Coates, Cordova, Tenn.
[73] Assignee: Wright Medical Technology, Inc., Arlington, Tenn.
[21] Appl. No.: 56,470
[22] Filed: May 3, 1993
[51] Int. Cl.$^6$ ............................................. A61F 2/38
[52] U.S. Cl. ......................................... 623/20; 623/18
[58] Field of Search ..................... 623/20, 18; 606/88
[56] References Cited

U.S. PATENT DOCUMENTS

| | | | |
|---|---|---|---|
| 4,822,365 | 4/1989 | Walker et al. | 623/20 |
| 4,822,366 | 4/1989 | Bolesky | 623/20 |
| 4,936,847 | 6/1990 | Manginelli | 623/20 |
| 5,152,796 | 10/1992 | Slamin | 623/20 |
| 5,176,684 | 1/1993 | Ferrante et al. | 606/86 |
| 5,181,925 | 1/1993 | Houston et al. | 623/20 |

FOREIGN PATENT DOCUMENTS

| | | | |
|---|---|---|---|
| 2006273 | 7/1990 | Canada . | |
| 0069683 | 1/1983 | European Pat. Off. | 623/20 |
| 0336774 | 10/1989 | European Pat. Off. . | |
| 2685633 | 7/1993 | France | 623/23 |
| 3922294 | 1/1991 | Germany | 623/20 |

Primary Examiner—David H. Willse
Attorney, Agent, or Firm—Walker, McKenzie & Walker

[57] ABSTRACT

A modular prosthetic femoral component for implantation upon the distal articular portion of a surgically prepared femur for articulating with an implanted complementary tibial component. A condylar component includes medial and lateral condyles, with an interposed trochlear notch and a patella guide interconnecting the medial and lateral condyles. A frustoconical primary receptacle extends from a proximal fixation surface of the condylar portion. A posterior stabilizing housing is disposed within the trochlear notch and includes a frustoconical post operatively engaged within the receptacle of the condylar portion. The posterior stabilizing housing may include a secondary frustoconical receptacle disposed in end-to-end fashion with the post for receiving a complementary distal end fitting on an elongated fixation stem. The distal end fitting of the stem is structured so that it is receivable into the primary receptacle of the condylar portion in the event the posterior stabilizing housing is not required.

19 Claims, 3 Drawing Sheets

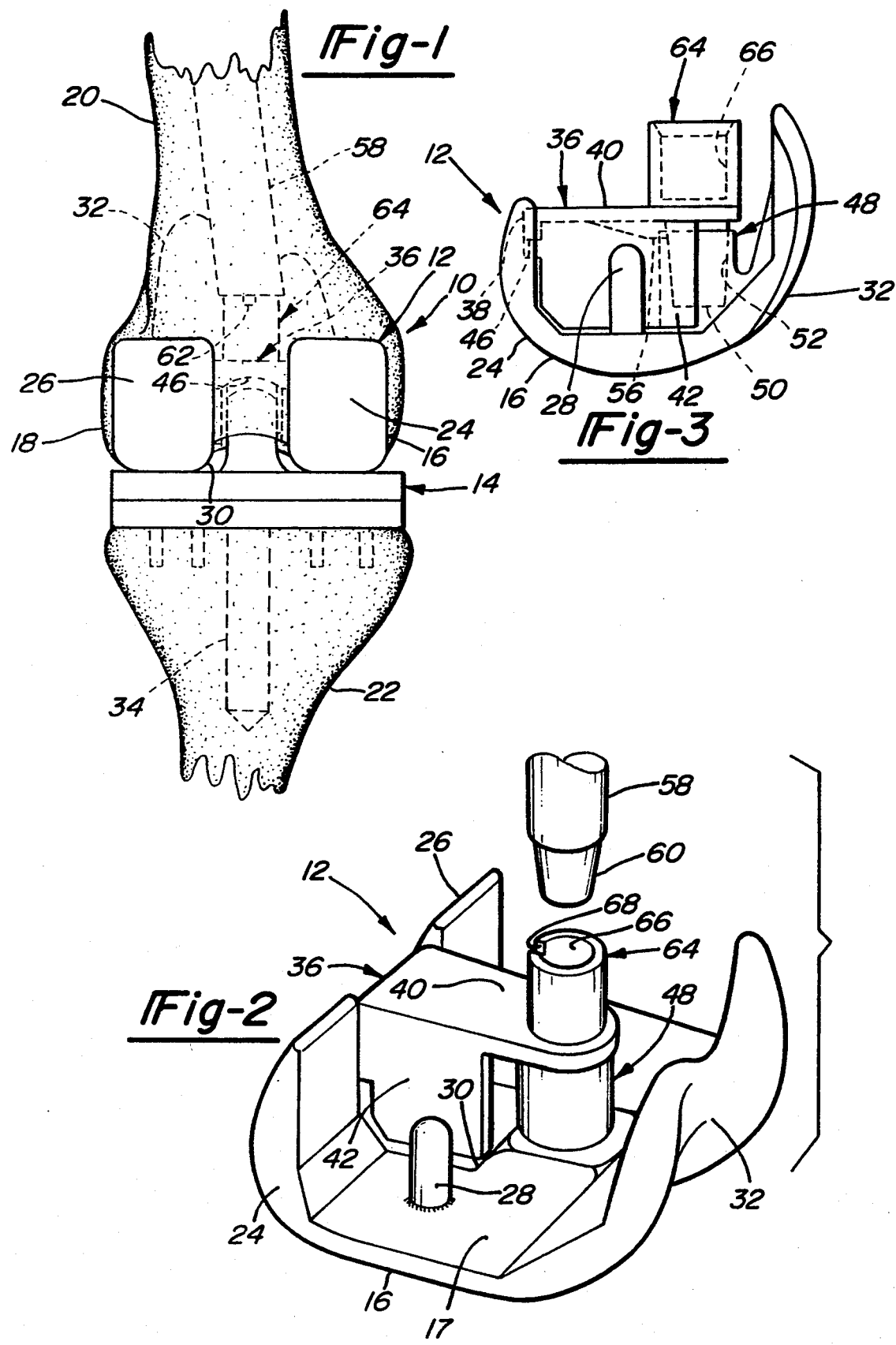

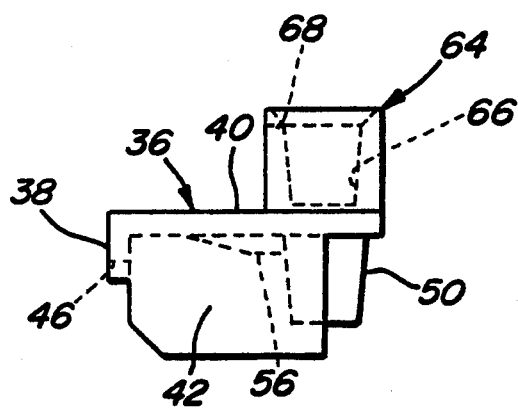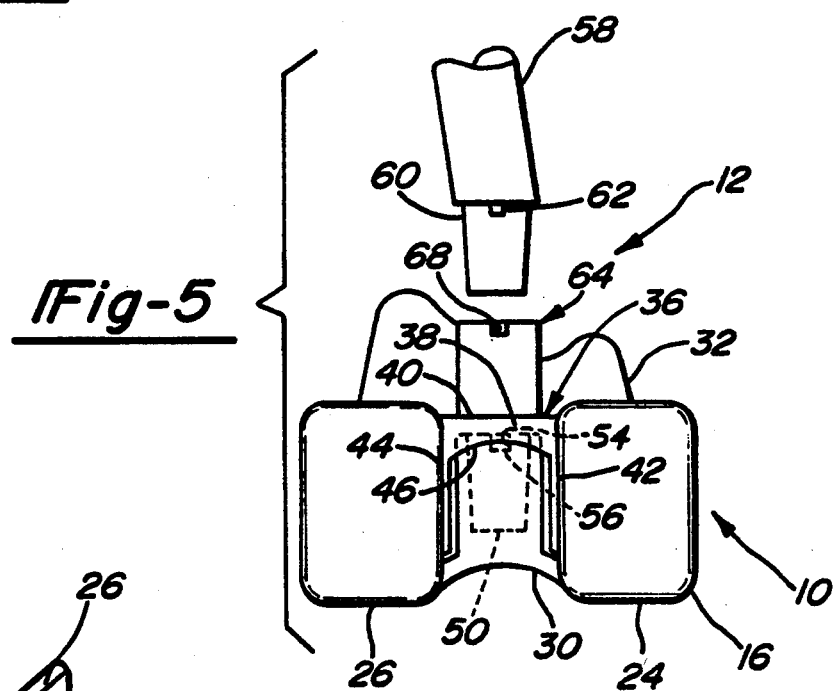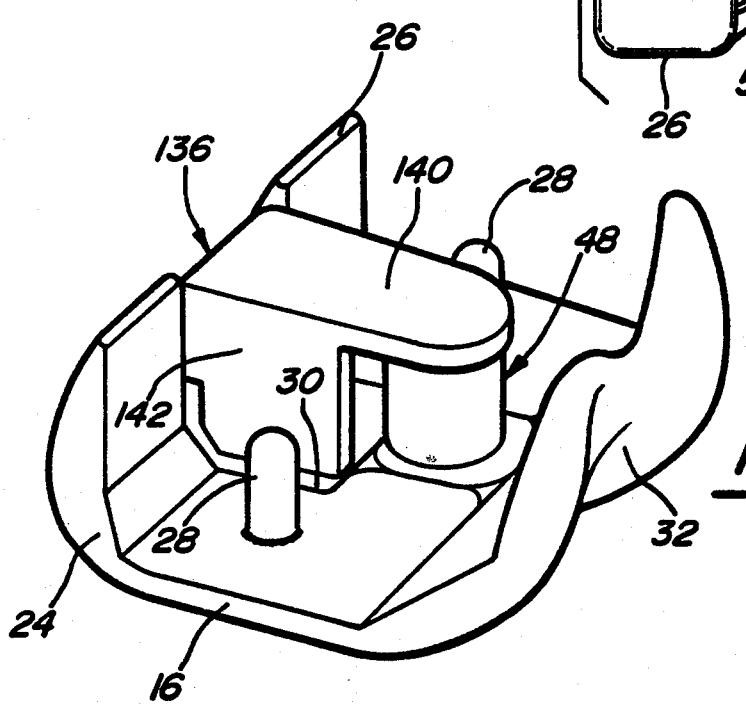

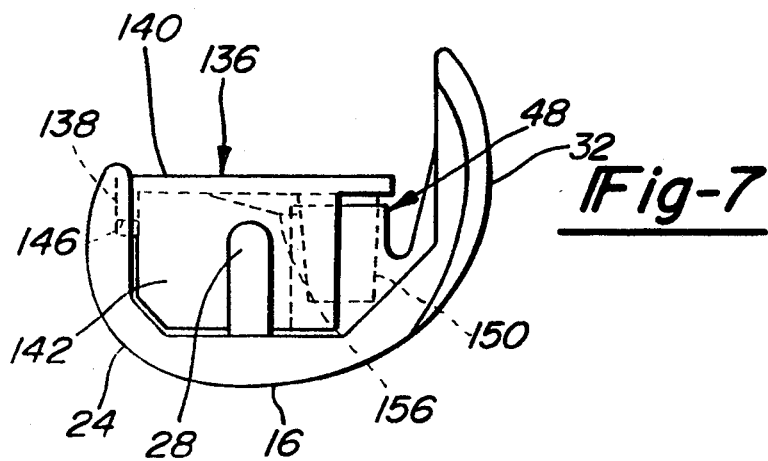
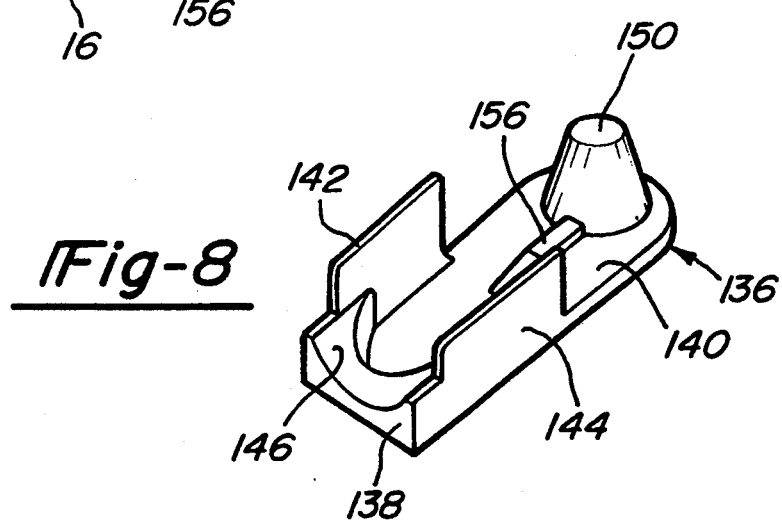
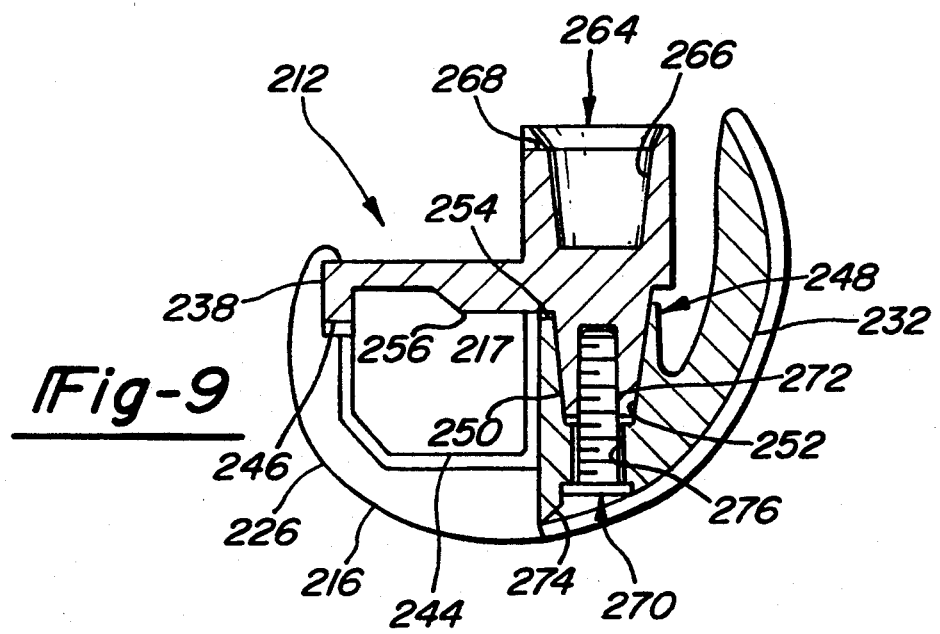

MODULAR FEMORAL IMPLANT

TECHNICAL FIELD

The invention relates generally to total knee arthroplasty utilizing surgically implantable knee joint prosthetic components. More specifically, the invention relates to a modular knee joint prosthetic component which is preoperatively convertible between a condylar type prosthesis, a posterior-stabilized prosthesis and either a condylar type or posterior-stabilized prosthesis having a fixation stem.

BACKGROUND ART

Knee arthroplasty is becoming more common to partially or totally replace knee joint components which have been damaged due to trauma or disease. Depending upon the condition of the ligaments and tendons surrounding the joint, a surgeon can select a prosthetic component which provides the necessary degree of stability to the knee joint. Provided the cruciate ligaments are sufficiently stable, a prosthesis can be selected which utilizes the natural soft tissue structures. This approach is preferred since the complex operation of the knee is most difficult to duplicate artificially.

A posterior-stabilized femoral prosthesis is indicated for a patient suffering from an unstable, painful knee joint where the instability is caused by the lack of or inadequacy of the posterior cruciate ligament. The posterior-stabilized knee joint consists of a tibial component having a stabilizing post protruding from the superior surface, or table, of the tibial component, and a femoral component with a posterior stabilizing housing to accept the stabilizing post and thereby provide the stability which the patient's knee joint lacks. Examples of posterior-stabilized total knee joint prosthesis may be had in U.S. Pat. Nos. 4,213,209, to Insall et al, issued Jul. 22, 1980, and 4,298,992, to Burstein et al, issued Nov. 10, 1981.

A mentioned above, if the patient's ligaments are sufficiently stabilized, a conventional condylar-stabilized component is preferably implanted, and the ligaments allowed to remain intact, thus resulting in a more natural and better functioning prosthesis. Even though satisfactory upon initial implantation surgery, the patient's ligaments may deteriorate over time so that they no longer adequately stabilize the artificial knee joint. Under these circumstances, revision surgery is necessary to convert the femoral component and tibial component of the prosthesis to a posterior-stabilized type, such as shown in U.S. Pat. No. 4,714,474, to Brooks, Jr. et al, issued Dec. 22, 1987, and assigned to the assignee of the subject invention, the disclosure of which is hereby expressly incorporated by reference and relied upon.

During revision surgery, the condylar-stabilized type of femoral component must be removed and replaced by a posterior-stabilized femoral component. Often, the femoral component includes an integral stem implanted and fixated within the femur, which stem must be removed from the femur resulting in considerable surgical trauma to the bone. European Patent Application Number 0336774, in the name of Richards Medical Company, published Oct. 11, 1989, discloses a modular femoral component having a detachable stem. Also, the Richards Medical prosthesis includes a modular posterior stabilizing housing which is detachable with respect to the modular stem. The primary disadvantage of the Richards Medical modular prosthesis resides in the manner in which the modular posterior stabilizing housing is attached to the condylar portion of the femoral components. More specifically, a pair of threaded posts extend proximally from the condylar portion and are received through corresponding apertures in the posterior stabilizing housing, such that a threaded portion of the posts extends above the posterior stabilizing housing. A pair of nuts are threadably engaged with the extending threaded portions of the posts and are tightened to fixedly retain the posterior stabilizing housing against the condylar portion.

The manner in which the Richards Medical modular posterior stabilizing housing is attached to the condylar portion presents numerous disadvantages. First, during implantation, the surgeon must resect corresponding portions of the bone to accommodate the two nuts which retain the posterior stabilizing housing to the condylar portion. Further, it is well known that threaded fasteners of the like disclosed by Richards Medical are prone to loosening over time thereby leading to premature failure of the prosthesis. Also, the nuts are prone to improper assembly, wherein the surgeon or other assembling personnel may inadvertently cross thread the nuts upon the threaded posts, thus further increasing the possibility of premature failure of the prosthesis. Also, such threaded fasteners are prone to fracture or other stress related failure due to the inherent non-uniform stress distribution in standard threaded fasteners. Further, the Richards Medical prosthesis is relatively expensive to produce and stock in that several inventory parts are required, i.e., modular posterior stabilizing housings in addition to a plurality of threaded fasteners.

SUMMARY OF THE INVENTION AND ADVANTAGES

A modular prosthetic femoral component is provided for implantation upon the distal articular portion and a surgically prepared femur for articulating with an implanted complementary component. The prosthesis comprises a condylar portion having a proximal fixation surface for fixed attachment to the surgically prepared surface of the distal femur. The condylar portion includes a medial condyle, a lateral condyle spaced from the medial condyle, a posteriorly extending trochlear notch disposed between the medial and lateral condyles, and a patella guide interconnecting the medial and lateral condyles and extending anteriorly from an intercondylar opening to the trochlear notch. A posterior stabilizing housing, separate and disjointed from the condylar portion, is provided for engaging and articulating with a posterior stabilizing post on the tibial component. A primary frustoconical adaptor means frictionally joins the posterior stabilizing housing and the proximal fixture surface of the condylar portion in force fit relation.

The subject invention overcomes the deficiencies inherent in the prior art by providing the primary frustoconical adaptor means which conveniently joins the posterior stabilizing housing to the condylar portion. The frustoconical adaptor means eliminates numerous additional components required by the prior art threaded fasteners. The force fit connection is not prone to stress related failures typical with prior art threaded fasteners, and thus extends the comparative useful life of

FIGURES IN THE DRAWINGS

Other advantages of the present invention will be readily appreciated as the same becomes better understood by reference to the following Detailed Description when considered in connection with the accompanying Drawings wherein:

FIG. 1 is a fragmentary perspective view of the subject prosthesis implanted upon a distal femur and coacting with a tibial component;

FIG. 2 is a perspective view of a femoral prosthesis of the subject invention;

FIG. 3 is a side view of the prosthesis of FIG. 2;

FIG. 4 is a side view of the posterior stabilizing housing of FIG. 3;

FIG. 5 is a posterior view of the prosthesis of FIG. 3 showing a modular stem posed for insertion into the secondary receptacle;

FIG. 6 is a perspective view as in FIG. 2 showing an alternative embodiment of the posterior stabilizing housing;

FIG. 7 is a side view of prosthesis of FIG. 6;

FIG. 8 is an inverted prospective view of the alternative modular posterior stabilizing housing according to the invention; and FIG. 9 is a cross-sectional view of yet another alternative embodiment of the subject invention.

DETAILED DESCRIPTION OF THE PREFERRED EMBODIMENT

Referring to the Figures, wherein like numerals indicate like or corresponding parts throughout the several views, a posterior stabilized total knee replacement prosthesis according to the subject invention is generally shown at 10 in FIGS. 1 and 2. The prosthesis 10 includes a femoral component, generally indicated at 12, disposed for articulating with a corresponding tibial component, generally indicated at 14. The femoral component 12 includes a condylar portion 16 implanted upon the prepared surface of a distal articular portion 18 of a human femur 20. The tibial component 14 is shown in FIG. 1 implanted upon the proximal articular surface of a tibia 22.

The condylar portion 16 includes a medial condyle 24 having a predetermined cam-like curvature for approximating the anatomical medial condyle. The condylar portion 16 also includes a lateral condyle 26 spaced from the medial condyle 24. The lateral condyle 26 is cam-like in curvature for approximating the anatomical lateral condyle. A post-like stake 28 extends from the superior surfaces of each of the medial 24 and lateral 26 condyles for anchoring the condylar portion 16 to the femur 20.

A posteriorly extending trochlear notch 30 is disposed between the medial 24 and lateral 26 condyles. The intercondylar trochlear notch 30 is positioned to approximate the trochlear notch found in anatomical femurs, and in the case of a natural ligament stabilized prosthesis, the trochlear notch 30 articulates on a button-like formation (not shown) extending upwardly, or superiorly, from the table of the tibial component 14.

The condylar portion 16 further includes a patella guide 32 formed integral with and interconnecting the medial 24 and lateral 26 condyles and extending anteriorly from the trochlear notch 30. The patella guide 32 forms a tongue-like appendage for contacting and guidably supporting either a natural or prosthetic patella (not shown).

A posterior-stabilized knee prosthesis is indicated for patients who suffer from a lack or inadequacy of the posterior cruciate ligament. For this purpose, the tibial component 14 includes a stabilizing post 34 protruding from the superior surface, or table, as shown in FIG. 1. Also, in a posterior-stabilized prosthesis 10, the femoral component 12 is provided with a posterior stabilizing housing, generally indicated at 36 in FIGS. 1–5. The posterior stabilizing housing 36 receives a stabilizing post 34 to provide the stability which the patient's natural ligaments lack. The posterior stabilizing housing 36 is movable into an operative position in the trochlear notch 30, i.e., between the medial 24 and lateral 26 condyles, and imbedded within the cancellous bone of the distal femur.

The posterior stabilizing housing 36 includes a posterior end wall 38 which is recessed superiorly with respect to the medial 24 and lateral 26 condyles for engaging the stabilizing post 34 on the tibial component 14. As is well known in the art, the posterior end wall 38 engages the stabilizing post 34 and thus stabilizes the femoral component 12 relative to the tibial component 14 during reflection of the knee.

Referring now to FIGS. 2–5, the posterior stabilizing housing 36 is shown including a generally flat ceiling portion 40 extending orthogonally from the posterior end wall 38. The ceiling portion 40 may include a textured or porous superior surface for enhancing adhesion with bone cement, or in the event bone cement is not used, promoting bone ingrowth. The posterior stabilizing housing 36 further includes a pair of side walls 42, 44 extending perpendicularly from the ceiling portion 40 on opposite sides of the posterior end wall 34. The side walls 42, 44 are respectively disposed adjacent the medial 24 and lateral 26 condyles of the femoral components 12. The sides walls 42, 44 may be stepped, or notched, adjacent to the posterior end wall 38. Preferably, the posterior end wall 38 includes an arcuate engagement surface 46 for better articulating with the stabilizing post 34 of the tibial component 14.

The femoral component 12 is of modular construction such that the condylar portion 16 may be used with or without the posterior stabilizing housing 36. For this reason, posterior stabilizing housing 36 is separate and disjointed from the condylar portion 16. Primary frustoconical adapter means, generally indicated at 48 in FIGS. 2–5, is provided for frictionally adjoining the posterior stabilizing housing 36 and the proximal fixation surface 17 of the condylar portion 16 in force-fit relation. Thus, the surgeon may determine whether a condylar stabilized or posterior stabilized femoral component 12 is required, and if the posterior stabilized femoral component is required, the posterior stabilizing housing 36 is quickly and securely connected to the condylar portion 16 by forcibly engaging the primary frustoconical adapter means 48.

The primary frustoconical adapter means 48 includes a frustoconical post 50 extending from the ceiling portion 40 of the posterior stabilizing housing 36, and a frustoconical primary receptacle 52 formed in the proximal fixation surface 17 of the condylar portion 16. Although, it will become apparent to those skilled in the art that the post 50 and primary receptacle 52 may be installed upon the other corresponding component to the same effect. The primary receptacle 52 extends generally parallel to the stakes 28 and is formed immediately anterior the trochlear notch 30.

The post 50 extends substantially perpendicularly from the ceiling portion 40 a distance slightly less than the extent of the side walls 42, 44. The frustoconical taper of the post 50 is designed to engage in surface-to-surface frictional contact with the primary receptacle 52 in wedge-like fashion similar to the conventionally known Morse taper.

The primary receptacle 52 is provided with an alignment groove 54 along its proximal edge. The alignment groove 54 extends radially outwardly from an imaginary center line passing through the primary receptacle 52. A key 56 extends radially outwardly from the post 50, along the ceiling portion 40, for engagement within the alignment groove 54 of the primary receptacle 52. When the key 56 is engaged within the alignment groove 54, the posterior stabilizing housing 36 is prevented from rotating relative to the condylar portion 16.

If, during implantation of the femoral component 12, it is determined that additional fixation is required, an elongated stem 58 may be installed in modular fashion to the condylar portion 16. The stem 58 extends into a canal prepared in the intramedullary portion of the femur 20, thus providing additional anchorage and support to the femoral component 12. The modular stem 58 is provided with a distal end fitting 60 for operative engagement with the primary frustoconical adapter means 48. More particularly, as best shown in FIGS. 1, 2 and 5, the distal end fitting 60 includes a male frustoconically tapering extension capable of being received in force-fit fashion into the primary receptacle 52. In this manner, the stem 58 can be attached to the condylar portion 16 when the femoral component 12 is implanted as a condylar-stabilized prosthesis (not shown). For this reason, the distal end fitting 60 is provided with a key 62 directly engagable with the alignment groove 54 of the primary receptacle 52 so as to prevent rotation of the stem 58 relative to the condylar portion 16.

However, if the surgeon determines that a posterior-stabilized prosthesis 10 is indicated, and it is desired to also utilize the stem 58, the posterior stabilizing housing 36 may include a secondary frustoconical adaptor means, generally indicated at 64 in FIGS. 2–5, for operatively engaging with the distal end fittings 60 of the stem 58. The secondary frustoconical adaptor means 64 comprises a secondary frustoconical receptacle 66 substantially matching the primary receptacle 52 of the condylar portion 16. The secondary receptacle 66 is also provided with an alignment groove 68 for receiving the key 62 of the stem 58 to prevent relative rotation therebetween.

As perhaps best shown in FIGS. 3 and 4, the secondary receptacle 66 and the post 50 are substantially coaxially aligned in end-to-end fashion on the posterior stabilizing housing 36. That is, the secondary receptacle 66 extends proximally from the ceiling portion 40 and the post 50 extends distally from the ceiling portion 40 directly below the secondary receptacle 66. In this manner, the stem 58 remains in the same orientation within the femur 20 regardless of whether the stem 58 is engaged in the secondary receptacle 66 (posterior-stabilized prosthesis) or the primary receptacle 52 (condylar-stabilized prosthesis).

Thus, according to the prosthesis 10 of this invention, the modular nature of the various components allow the surgeon to determine during the implantation operation whether a condylar-stabilized prosthesis is indicated and whether such prosthesis should include a stem 58, or in the alternative whether a posterior-stabilized prosthesis is indicated and whether such prosthesis should include a stem 58.

ALTERNATIVE EMBODIMENT OF FIGS. 6–8

Referring to FIGS. 6–8, an alternative embodiment of the posterior stabilizing housing is shown and described. Referring to the posterior stabilizing housing, like structural features are designated with reference numbers corresponding to those used above but with the numeral suffix "1" added for clarity. This alternative embodiment of the posterior stabilizing housing 136 is intended for use only when the stem 58 is not required. That is to say, the alternative posterior stabilizing housing 136 is not compatible with the stem 58.

The alternative posterior stabilizing housing 136 is distinguished from that of the preferred embodiment by the elimination of the secondary frustoconical adaptor means 64, and more particularly elimination of the secondary receptacle 66. Thus, the superior surface of the ceiling portion 140 is unincumbered by the secondary receptacle 66. Thus, when employed as a posterior-stabilized prosthesis, the stem 58 can not be used.

ALTERNATIVE EMBODIMENT OF FIG. 9

In FIG. 9, yet another alternative embodiment of the posterior stabilizing housing is illustrated. FIG. 9, like structural features are designated with reference numbers corresponding to those used above with the numerical suffix "2" added for clarity.

This alternative posterior stabilizing housing 236 differs from the preferred embodiment in that a supplemental binder means, generally indicated at 270, for preventing disconnection of the primary frustoconical adapter means 248. Preferably, the supplemental binder means 270 includes a threaded fastener 272 for locking the post 250 within the primary receptacle 252. However, the supplemental binder means 270 may take other forms, such as a simple pin type connection, e.g., a modified cotter pin arrangement, etc.

The femoral component 212 is provided with a counter bore 274 and a clearance hole 276 to accommodate the fastener 272. The clearance hole 276 extends between the trochlear notch 230 and the primary receptacle 252, with the counter bore 274 being formed adjacent the trochlear notch 230. In this manner, the head of the fastener 272 is seated within the counter bore 274 in a noninterfering position with the patella (not shown). The post 250 is provided with a threaded bore for receiving the fastener 272. The threaded bore and the post 250 aligned with the clearance hole 276 in the femoral component 212. Hence, in effect, the fastener 272 is buttressed against the primary receptacle 252, i.e., the femoral component 212, and threadably engaged with the post 250 for locking the two members of the primary frustoconical adapter means 248 in an engaged operative position. In this manner, all benefits of the mating frustoconical portions, described below, are retained, while the supplemental binder means 270 operates to prevent inadvertent disconnection of the two components.

The subject prosthesis 10 is particularly advantageous in that relatively few components are required to transform the prosthesis between a condylar-stabilized femoral component 12, a condylar stabilized femoral component 12 with a stem 58, a posterior-stabilized femoral component 12, and a posterior-stabilized femoral component 12 with a stem 58. Also, modification of the femoral component 12 between the various permutations is quickly and easily accomplished by the surgeon without the necessity for special tools or additional fasteners. Additionally, the frustoconically mating portions between the modular components provides a structurally stable connection which is not susceptible to the fatigue and stress related failures of threaded fasteners. And, the femoral modular component requires fewer inventory parts and therefore reduces the overall costs of the prosthesis 10.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically described.

What is claimed is:

1. A modular prosthetic femoral component for implantation upon the distal articular portion of a surgically prepared femur for articulating with an implanted complementary tibial component, the femoral component comprising: a condylar portion having a proximal fixation surface for fixed attachment to the surgically prepared surface of the distal femur; the condylar portion including a medial condyle, a lateral condyle spaced from the medial condyle, a posteriorly extending trochlear notch disposed between the medial and lateral condyles, and a patella guide interconnecting the medial and lateral condyles and extending anteriorly from an intercondylar opening to the trochlear notch; a posterior stabilizing housing separate and disjoined from the condylar portion for engaging an articulating posterior stabilizing post on the tibial component; the posterior stabilizing housing including a posterior end wall for engaging the articulating posterior stabilizing post when the femoral component and tibial component are reflected to stabilize the femoral component relative to the tibial component and forming a posterior stabilizing post receptacle to accept the articulating posterior stabilizing post; and primary frustoconical adapter means for frictionally joining the posterior stabilizing housing and the proximal fixation surface in force fit relation.

2. A prosthesis as set forth in claim 1 wherein the primary frustoconical adaptor means includes a frustoconical post extending from one of the proximal fixation surface and posterior stabilizing housing, and a frustoconical primary receptacle disposed in the other of the proximal fixation surface and the posterior stabilizing housing.

3. A prosthesis as set forth in claim 2 further including an elongated stem having a distal end fitting for operative engagement with the primary frustoconical adapter means.

4. A prosthesis as set forth in claim 3 wherein the posterior stabilizing housing includes a secondary frustoconical adapter means disposed for operatively engaging the distal end fitting of the stem.

5. A prosthesis as set forth in claim 4 wherein the primary receptacle is disposed on the proximal fixation surface and the post is disposed on the posterior stabilizing housing.

6. A modular prosthetic femoral component for implantation upon the distal articular portion of a surgically prepared femur for articulating with an implanted complementary tibial component, the femoral component comprising a condylar portion having a proximal fixation surface for fixed attachment to the surgically prepared surface of the distal femur; the condylar portion including a medial condyle, a lateral condyle spaced from the medial condyle, a posteriorly extending trochlear notch disposed between the medial and lateral condyles, and a patella guide interconnecting the medial and lateral condyles and extending anteriorly from an intercondylar opening to the trochlear notch;

a posterior stabilizing housing separate and disjoined from the condylar portion for engaging an articulating posterior stabilizing post on the tibial component;

primary frustoconical adapter means for frictionally joining the posterior stabilizing housing and the proximal fixation surface in force fit relation; the primary frustoconical adaptor means including a frustoconical post extending from one of the proximal fixation surface and posterior stabilizing housing, and a frustoconical primary receptacle disposed in the other of the proximal fixation surface and the posterior stabilizing housing; and an elongated stem having a distal end fitting for operative engagement with the primary frustoconical adapter means; wherein the posterior stabilizing housing includes a secondary frustoconical adapter means disposed for operatively engaging the distal end fitting of the stem;

the primary receptacle is disposed on the proximal fixation surface and the post is disposed on the posterior stabilizing housing; and the secondary frustoconical adapter means comprising a secondary frustoconical receptacle matching the primary receptacle of the condylar portion.

7. A prosthesis as set forth in claim 6 wherein the secondary receptacle and the post are substantially coaxially aligned in end-to-end fashion on the posterior stabilizing housing.

8. A prosthesis as set forth in claim 7 wherein the posterior stabilizing housing includes a posterior end wall recessed superiorly with respect to the medial and lateral condyles.

9. A prosthesis as set forth in claim 8 wherein the posterior end wall includes an arcuate engagement surface.

10. A prosthesis as set forth in claim 9 wherein the posterior stabilizing housing includes a ceiling portion and a pair of side walls extending from the ceiling portion on opposite sides of the posterior end wall and respectively disposed adjacent the medial and lateral condyles.

11. A prosthesis as set forth in claim 10 wherein the secondary receptacle extends proximally from the ceiling portion and the post extends distally from the ceiling portion.

12. A modular prosthetic femoral component for implantation upon the distal articular portion of a surgically prepared femur for articulating with an implanted complementary tibial component, the femoral component comprising a condylar portion having a proximal fixation surface for fixed attachment to the surgically prepared surface of the distal femur; the condylar portion including a medial condyle, a lateral condyle spaced from the medial condyle, a posteriorly extending trochlear notch disposed between the medial and lateral condyles, and a patella guide interconnecting the medial and lateral condyles and extending anteriorly from an intercondylar opening to the trochlear notch;

a posterior stabilizing housing separate and disjoined from the condylar portion for engaging an articulating posterior stabilizing post on the tibial component;

primary frustoconical adapter means for frictionally joining the posterior stabilizing housing and the proximal fixation surface in force fit relation; the primary frustoconical adaptor means including a frustoconical post extending from one of the proximal fixation surface and posterior stabilizing housing, and a frustoconical primary receptacle disposed in the other of the proximal fixation surface and the posterior stabilizing housing; and an elongated stem having a distal end fitting for operative engagement with the primary frustoconical adapter means; wherein the posterior stabilizing housing includes a secondary frustoconical adapter means disposed for operatively engaging the distal end fitting of the stem;

the secondary frustoconical adapter means comprises a secondary frustoconical receptacle matching the primary receptacle of the condylar portion; and each of the primary receptacle and secondary receptacle including an alignment groove, and each of the post and distal end fitting including a key engagable within the corresponding alignment groove.

13. A prosthesis as set forth in claim 12 further including supplemental binder means for preventing disconnection of the primary frustoconical adapter means.

14. A prosthesis as set forth in claim 13 wherein the supplemental binder means includes a threaded fastener.

15. A prosthesis as set forth in claim 14 wherein the fastener is buttressed against the primary receptacle and threadably engages the post.

16. A prosthesis as set forth in claim 15 wherein the primary receptacle is disposed on the proximal fixation surface and the post is disposed on the posterior stabilizing housing.

17. A prosthesis as set forth in claim 16 wherein the femoral component includes a counter bore and a clearance hole extending between the trochlear notch and the primary receptacle.

18. A modular prosthetic femoral component for implantation upon the distal articular portion of a surgically prepared femur for articulating with an implanted complementary tibial component, the femoral component comprising: a condylar portion having a proximal fixation surface for fixed attachment to the surgically prepared surface of the distal femur; the condylar portion including a medial condyle, a lateral condyle spaced from the medial condyle, a posteriorly extending trochlear notch disposed between the medial and lateral condyles, and a patella guide interconnecting the medial and lateral condyles and extending anteriorly from an intercondylar opening to the trochlear notch; a posterior stabilizing housing separate and disjointed from the condylar portion for engaging an articulating posterior stabilizing post on the tibial component; the posterior stabilizing housing including a posterior end wall for engaging the articulating posterior stabilizing post when the femoral component and tibial component are reflected to stabilize the femoral component relative to the tibial component and forming a posterior stabilizing post receptacle to accept the articulating posterior stabilizing post; an elongated stem having a distal end fitting; and primary frustoconical adapter means for frictionally joining any one of the posterior stabilizing housing and the distal end fitting of the stem to the proximal fixation surface of the condylar portion in force-fit relation.

19. A modular prosthetic femoral component for implantation upon the distal articular portion of a surgically prepared femur for articulating with an implanted complementary tibial component, the femoral component comprising: a condylar portion having a proximal fixation surface for fixed attachment to the surgically prepared surface of the distal femur; the condylar portion including a medial condyle, a lateral condyle spaced from the medial condyle, a posteriorly extending trochlear notch disposed between the medial and lateral condyles, and a patella guide interconnecting the medial and lateral condyles and extending anteriorly from an intercondylar opening to the trochlear notch; a posterior stabilizing housing separate and disjointed from the condylar portion for engaging an articulating posterior stabilizing post on the tibial component; the posterior stabilizing housing including a frustoconically tapering post extending therefrom; an elongated stem having a frustoconically tapering distal end fitting; and a primary frustoconical receptacle extending from the proximal fixation surface of the condylar portion for receiving any one of the post of the posterior stabilizing housing and the distal end fitting of the stem in force fit relation.

* * * * *